(12) United States Patent
Imai

(10) Patent No.: US 6,726,937 B2
(45) Date of Patent: Apr. 27, 2004

(54) ANTIFUNGAL COMPOSITION

(75) Inventor: Hiroshi Imai, Osaka (JP)

(73) Assignee: Shinto Fine Co., Ltd., Osaka (JP)

( * ) Notice: Subject to any disclaimer, the term of this patent is extended or adjusted under 35 U.S.C. 154(b) by 0 days.

(21) Appl. No.: 10/184,962

(22) Filed: Jul. 1, 2002

(65) Prior Publication Data

US 2003/0031729 A1 Feb. 13, 2003

(30) Foreign Application Priority Data

Jul. 3, 2001 (JP) .................................. 2001-201563

(51) Int. Cl.[7] ................ A01N 59/20; A01N 43/80; A01N 43/647; A01N 43/653

(52) U.S. Cl. ................ 424/635; 424/630; 424/631; 424/632; 424/633; 424/634; 424/637; 424/638; 514/359; 514/372; 514/373; 514/383; 514/384; 514/385; 514/403

(58) Field of Search ................ 514/372, 373, 514/383, 384, 499, 500, 359, 385, 403; 424/630–635, 637–638, DIG. 11

(56) References Cited

U.S. PATENT DOCUMENTS 5,186,947 A * 2/1993 Goettsche et al. .......... 424/638
5,364,649 A * 11/1994 Rossmoore et al. ........ 424/637
5,397,795 A 3/1995 Valcke ....................... 514/383
6,339,081 B1 * 1/2002 Payne ......................... 514/184

FOREIGN PATENT DOCUMENTS

| DE | 196 49 482 A1 | 6/1997 |
| EP | 0 864 406 A2 | 9/1998 |
| EP | 0 864 406 A3 | 9/1998 |
| JP | 10-298012 | 11/1998 |
| JP | 2001-192308 | 7/2001 |
| WO | 00/69265 | 11/2000 |

* cited by examiner

*Primary Examiner*—John Pak
(74) *Attorney, Agent, or Firm*—Birch, Stewart, Kolasch & Birch, LLP

(57) ABSTRACT

The present invention provides use of a composition containing 2-n-octyl-4-isothiazolin-3-one and N-n-butyl-1,2-benzisothiazolin-3-one for providing antifungal efficacy to a wood preservative containing copper oxide or a copper salt and a fungicidal azole. It also provides a wood preservative which comprises 2-n-octyl-4-isothiazolin-3-one, N-n-butyl-1,2-benzisothiazolin-3-one, copper oxide or a copper salt, and a fungicidal azole as active ingredients.

6 Claims, No Drawings

ANTIFUNGAL COMPOSITION

FIELD OF THE INVENTION

This invention relates to antifungal compositions for wood protection. More particularly, this invention provides an improvement for adding antifungal efficacy to a wood preservative containing copper and an azole fungicide, and also provides an antifungal composition which can be used as a pressure process type product for wood preservatives.

BACKGROUND ART

In order to protect wood timbers, the wood preservative products comprising copper (oxide or salts) and a fungicidal azole as major components are diluted to 25 to 50 folds with water and injected into the timber under high pressure. As the injected volume of the products is generally 200 to 500 kg/m$^3$, it takes a long period until the timber dries. By the occurrence of mold on the surface of the timber during the period, the quality of the timber becomes worse and the marketability significantly decreases. In order to solve such a problem, fungicides may be added into the treating solution of the wood preservative mentioned above before injection. Although a lot of fungicides for timbers are on the market, these fungicides could not be used for this purpose. The reason is that the conventional fungicides are not solved or dispersed in the wood preservative solution, or that the wood preservative products mentioned above such as containing inorganic ion and alkaline tend to decompose in the solution. Among the conventional fungicides, 4-chloro-2-methylisothiazolin-3-one (hereinafter, referred as to CMIT) which is water-soluble and effective against mold is only used. However, as CMIT is corrosive to metal, it caused the damage to injection vessel, pump, pipe and the other instruments. As the above-mentioned wood preservative products are alkaline, CMIT is gradually decomposed and the concentration becomes lower. Maintaining the concentration of CMIT in the process of injection is very difficult, and further use of CMIT is not economical because of the necessity of frequent addition of CMIT.

This invention was made to solve the above-mentioned problems such as fungicidal activity, operability, corrosiveness to metal and economical problem.

SUMMARY OF THE INVENTION

The present invention provides use of a composition containing 2-n-octyl-4-isothiazolin-3-one (hereinafter, referred as to OIT) and N-n-butyl-1,2-benzisothiazolin-3-one (hereinafter, referred as to BBIT) for providing antifungal efficacy to a wood preservative containing copper oxide or a copper salt and a fungicidal azole. Further, it provides a method for providing antifungal efficacy to a wood preservative containing copper oxide or a copper salt and a fungicidal azole which comprises adding a composition containing OIT and BBIT to the wood preservative. Furthermore, it provides a wood preservative which comprises OIT, BBIT, copper oxide or a copper salt, and a fungicidal azole as active ingredients.

According to the present invention, an addition of OIT and BBIT to a wood preservative gives high antifungal activity with good operability and without corrosive to metal when the mixture can be used as pressure process type wood preservative products.

DETAILED DESCRIPTION OF THE INVENTION

The wood preservative containing copper and a fungicidal azole is known and available on the market.

The copper is usually contained in the wood preservative as cupric oxide or cupric salts such as sulfate, chloride, bromide, nitrate and so on.

The fungicidal azoles are well-known in the references such as "The Pesticide Manual 10th Edition" published by British Crop Protection Council (1994), "Shibuya Index 8th Edition" published by Shibuya Index Research Group (1999) and so on. Typical examples of the fungicidal azoles include tebuconazole, cyproconazole, hexaconazole and so on. These fungicidal azoles are generally effective for controlling Basidiomycota, but less effective against the mold such as Aspergillus spp., Cladosporium spp., Penicillium spp. and so on. Thus the addition of OIT and BBIT to the wood preservative gives excellent antifungal efficacy against Aspergillus spp., Cladosporium spp., Penicillium spp., Aureobasidium spp., Fusarium spp. and so on.

The wood preservative may contain further termiticidal component such as boric acid, organophosphorus compounds, carbamate compounds, pyrethroid compounds, neonicotinoid compounds and so on.

Both of OIT and BBIT used in this invention are widely utilized as bactericide and fungicide, and they are available on the market.

In the present invention, use of OIT and BBIT at the weight ratio of 1:19 to 19:1 is preferable in view of synergistic effect. The weight ratio is more preferably 1:9 to 9:1.

When OIT and BBIT are added to the wood preservative, the composition comprising OIT and BBIT as active ingredients is usually utilized. The composition may be a simple mixture of OIT and BBIT, but preferably formulations (e.g., emulsifiable concentrate, suspensible concentrate, water-soluble formulation, solution) further containing inert carrier or auxiliary. The inert carriers are exemplified by hydrophilic solvents such as alcohols, glycols, glycol-ethers and ketones, and hydrophobic solvents such as aliphatic hydrocarbons, aromatic hydrocarbons and esters. The auxiliaries are exemplified by nonionic surfactants and anionic surfactants. The formulations can be prepared by known methods. For example, the water-soluble formulations can be prepared by dissolving OIT and BBIT in the above-mentioned hydrophilic solvents, and the emulsifiable concentrates can be prepared by dissolving OIT and BBIT in the above-mentioned hydrophobic solvents with a nonionic surfactant or anionic surfactant.

The composition containing OIT and BBIT significantly gives excellent antifungal activity in comparison with OIT or BBIT solely. Further, it is extremely less corrosive to metal than CMIT, and shows long residual activity than CMIT. So, the composition is easy to be handled and is very economical.

The present invention also provides a wood preservative which comprises OIT, BBIT, copper oxide or a copper salt, and a fungicidal azole as active ingredients. The wood preservative is usually prepared by adding a mixture of OIT and BBIT or formulation thereof to a wood preservative containing copper oxide or a copper salt and a fungicidal azole. The wood preservative is usually aqueous solution, emulsion or suspension, and the weight ratio of OIT and BBIT in the wood preservative is usually 1:19 to 19:1, preferably 1:9 to 9:1. Each content of OIT, BBIT, copper oxide or a copper salt, and a fungicidal azole is usually 0.01–30%, 0.01–30%, 50% or more, and 0.01–30% by weight, respectively.

The wood preservative is generally applied into timber at the volume of 200 to 500 kg/m$^3$ by injection under high pressure.

EXAMPLE

The following examples and test examples of the present invention are set forth, by way of illustration but the present invention does not limited to the examples. In these examples, percentages and parts are by weight unless specified otherwise, and names of the compounds used therein are abbreviated as in the following.

Formulation Examples

TABLE 1

|  | Formulation Example 1 | Formulation Example 2 | Formulation Example 3 | Comparison Example 1 | Comparison Example 2 | Comparison Example 3 |
|---|---|---|---|---|---|---|
| OIT | 1.0 | 5.0 | 9.0 | 10.0 | | |
| BBIT | 9.0 | 5.0 | 1.0 | | 10.0 | |
| CMIT | | | | | | 10.0 |
| Solvent *1 | 85.0 | 85.0 | 85.0 | 85.0 | 85.0 | 85.0 |
| Surfactant *2 | 5.0 | 5.0 | 5.0 | 5.0 | 5.0 | 5.0 |
| Total | 100.0 | 100.0 | 100.0 | 100.0 | 100.0 | 100.0 |

*1: Solvent: diethyleneglycolmonobutylether
*2: Surfactant: Polyoxyalkylenealkylether

Test Example 1

Pressure process type wood preservative (Tanaris CuAz, containing cupric oxide and azole (tebuconazole) as the active ingredients, manufactured by Hycson Inc.) was diluted to 30 folds by water. Then the predetermined concentrations of formulation examples 1 to 3 and comparison examples 1 to 3 were added therein. Half of each solution was injected by pressure process to the timber (western hemlock, 10 cm×10 cm×30 cm). The other half was kept at the room temperature for one month, and then injected same as above. The amount of the injected solution was more than 250 kg/m³ in wood. The treated timbers were kept for one night, and cut out to 5 cm×5 cm×1 cm. These wood pieces were used for antifungal experiment. Each specimen was placed on a potato dextrose agar plate, and 1 ml of a mixed fungus spore was sprayed over the specimen, followed by culturing at 28 degree C. and at 95% in relative humidity for 2 months. The test strains used were *Aspergillus niger*, *Cladosporium cladosporioides*, *Penicillium funiculosum*, *Aureobasidium pullulans*, *Gliocladium virens* and *Fusarium sp.* The results obtained are shown in Table 2. In the table, the degree of fungus growth was determined according to the following ratings.

(−) No fungus growth is observed at all on the specimen.
(+) Fungus has grown only on the side surface of said specimen.
(++) The area of the specimen in which fungus has grown is 1/10 to 1/3 of the total area of said specimen.
(+++) The area of the specimen on which the fungus has grown exceeds 1/3 of the total area of said specimen.

TABLE 2

| Composition | concentration (%) | Treated just after preparing Culturing period | | Treated at 30 days after preparing Culturing period | |
|---|---|---|---|---|---|
| | | 30 days | 60 days | 30 days | 60 days |
| Untreated | 0 | +++ | +++ | +++ | +++ |
| Formulation Example 1 | 0.05 | − | + | − | ++ |
| | 0.10 | − | + | − | + |
| | 0.15 | − | − | − | − |
| | 0.20 | − | − | − | − |
| Formulation Example 2 | 0.05 | − | − | − | + |
| | 0.10 | − | − | − | + |
| | 0.15 | − | − | − | − |
| | 0.20 | − | − | − | − |
| Formulation Example 3 | 0.05 | − | + | − | + |
| | 0.10 | − | − | − | + |
| | 0.15 | − | − | − | − |
| | 0.20 | − | − | − | − |
| Comparison Example 1 | 0.05 | + | ++ | + | ++ |
| | 0.10 | + | + | + | + |
| | 0.15 | − | + | − | + |
| | 0.20 | − | + | − | + |
| Comparison Example 2 | 0.05 | ++ | ++ | ++ | +++ |
| | 0.10 | + | ++ | ++ | +++ |
| | 0.15 | + | + | + | ++ |
| | 0.20 | − | + | − | + |
| Comparison Example 3 | 0.05 | − | + | +++ | +++ |
| | 0.10 | − | − | +++ | +++ |
| | 0.15 | − | − | ++ | ++ |
| | 0.20 | − | − | ++ | ++ |

As is clear from the results shown in Table 2, a marked antifungal activity of the formulation examples 1 to 3 of the present invention was observed in comparison with that of comparison examples 1 and 2. Comparison example 3 showed high antifungal activity at the case of just after preparing, however, the activity decreased remarkably at the cases where the solution was kept for 30 days.

Pressure process type wood preservative (Tanaris CuAz, manufactured by Hycson Inc.) was diluted to 30 folds by water, and 0.2% of formulation example 2 and comparison example 3 were added therein. Polished iron piece (25 mm×25 mm×2 mm) was immersed therein for 2 months and the corrosive grade of the iron was observed. The result was shown in Table 3.

TABLE 3

| | Decrease of weight (mg/cm²) | Appearance of iron piece | Appearance of test solution |
|---|---|---|---|
| Formulation example 2 | −0.02 | Normal | Normal |
| Comparison example 3 | −0.20 | Occurrence of spotted stain | Slightly change to green |

Formulation example 2 of the present invention was not corrosive to iron and showed no abnormality to the test solution, however, comparison example 3 was corrosive to iron and showed the tendency to change the quality of the solution.

What is claimed is:

1. A method for providing antifungal efficacy to a wood preservative containing copper oxide or a copper salt and a fungicidal azole which comprises adding a composition containing 2-n-octyl-4-isothiazolin-3-one and N-n-butyl-1,2-benzisothiazolin-3-one to the wood preservative.

2. A wood preservative which comprises 2-n-octyl-4-insothiazolin-3-one, N-n-butyl-1,2-benzisothiazolin-3-one, copper oxide or a copper salt, and a fungicidal azole as active ingredients.

3. A wood preservative according to claim 2, wherein the fungicidal azole is tebuconazole, cyproconazole or hexaconazole.

4. A wood preservative according to claim 2, wherein the weight ratio of 2-n-octyl-4-isothiazolin-3-one and N-n-butyl-1,2-benzisothiazolin-3-one is 1:19 to 19:1.

5. A wood preservative according to claim 2, wherein the weight ratio of 2-n-octyl-4-isothiazolin-3-one and N-n-butyl-1,2-benzisothiazolin-3-one is 1:9 to 9:1.

6. A wood preservative according to claim 2, wherein the content of the 2-n-octyl-4-isothiazolin-3-one, N-n-butyl-1,2-benzisothiazolin-3-one, copper oxide or copper salt, and the fungicidal azole is 0.01–30%, 0.01–30%, 50% or more, and 0.01–30% by weight, respectively.

* * * * *